Figure 1:
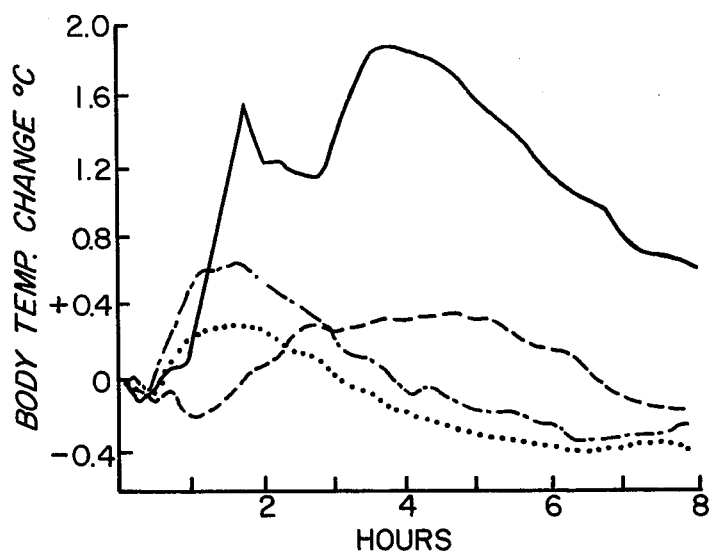
Figure 2:
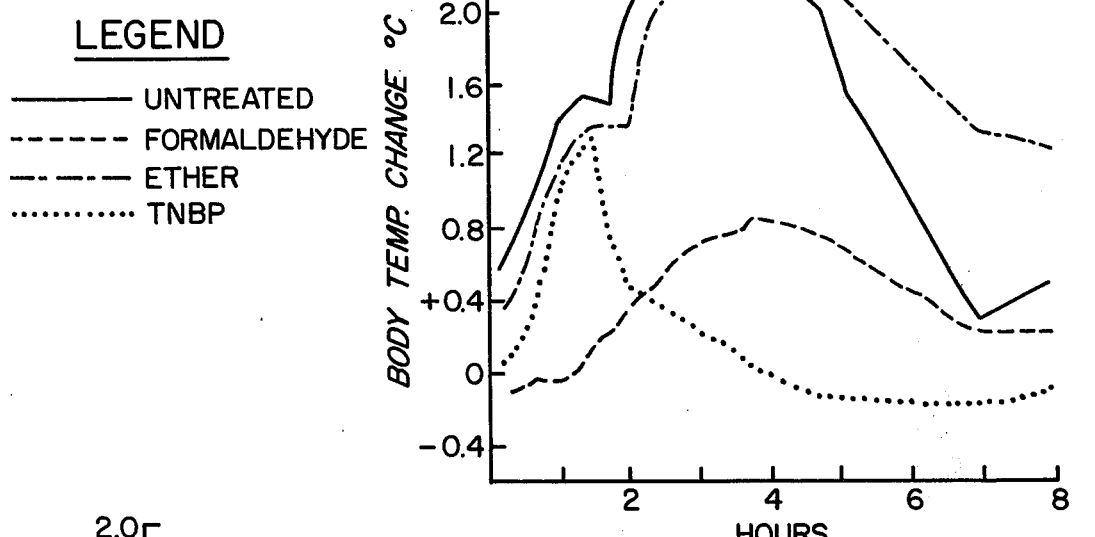
Figure 3:
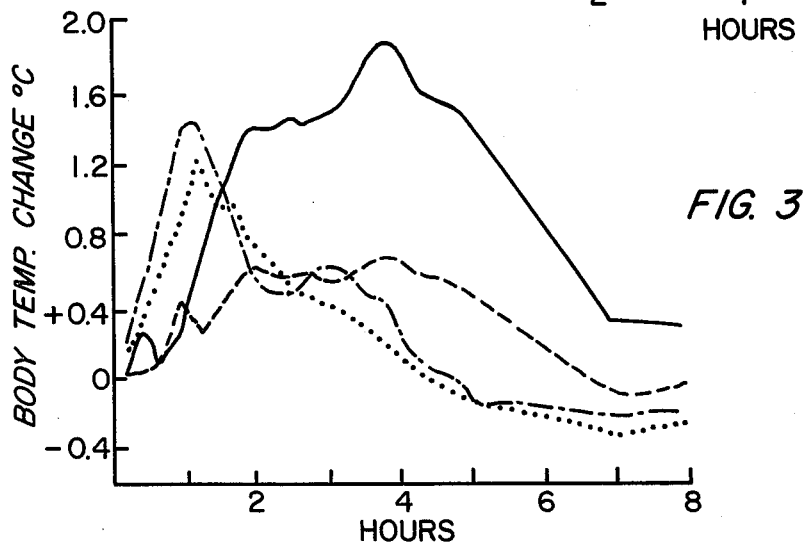

United States Patent [19]

Neurath

[11] 3,962,421

[45] June 8, 1976

[54] METHOD FOR THE DISRUPTION OF LIPID-CONTAINING VIRUSES

[75] Inventor: Alexander R. Neurath, Philadelphia, Pa.

[73] Assignee: American Home Products Corporation, New York, N.Y.

[22] Filed: Sept. 19, 1974

[21] Appl. No.: 507,306

Related U.S. Application Data

[63] Continuation of Ser. No. 370,906, June 18, 1973, abandoned, which is a continuation of Ser. No. 201,937, Nov. 24, 1971, abandoned, which is a continuation-in-part of Ser. No. 134,935, April 19, 1971, abandoned, which is a continuation-in-part of Ser. No. 826,783, May 16, 1969, abandoned.

[52] U.S. Cl. ................................................. 424/89
[51] Int. Cl.² .................. A61K 39/18; A61K 39/29
[58] Field of Search ......................... 195/1.4; 424/89

[56] References Cited

OTHER PUBLICATIONS

Webster et al. – J. Immunology (vol. 96), pp. 596–605 (1966).

*Primary Examiner*—Sam Rosen
*Attorney, Agent, or Firm*—Robert Wiser

[57] ABSTRACT

Virus-containing media are treated and the viruses broken down into sub-units by mixing with trialkyl phosphates in the presence of a wetting agent. In comparison with conventional means, sub-unit vaccines prepared therefrom have low toxic pyrogen content, and influenza viruses of Types A and B are disrupted without substantial decreases in neuraminidase level. The method can be used on viruses contained in relatively dilute allantoic fluids as well as those in concentrated centrifugates.

16 Claims, 3 Drawing Figures

LEGEND
— UNTREATED
--- FORMALDEHYDE
-·- ETHER
···· TNBP

METHOD FOR THE DISRUPTION OF LIPID-CONTAINING VIRUSES

This application is a continuation of U.S. patent application Ser. No. 370,906, filed June 18, 1973, which is a continuation of U.S. patent application Ser. No. 201,937, filed Nov. 24, 1971, which is a continuation-in-part of U.S. patent application Ser. No. 134,935, filed Apr. 19, 1971, which is a continuation-in-part of U.S. patent application Ser. No. 826,783, filed May 16, 1969, all now abandoned.

This application relates to the treatment of viruses useful in the preparation of vaccines. More particularly, it relates to the disruption of viruses into sub-units especially useful to prepare potent immunizing agents.

BACKGROUND OF THE INVENTION

There has long been a need for satisfactory methods of disrupting viruses, especially lipid-containing viruses, for example, the viruses of influenza, Newcastle disease, rabies, and the like. Available methods for the production of virus antigens involve isolation of virus from natural sources or following propagation of virus in fowl embryo cell fluids, tissue culture fluids and similar aqueous media.

The viruses formed in these media consist of discrete particles, which contain, for example, bound-in lipids. More recently, improved vaccines have been prepared by disrupting the intact viruses into sub-units, which are still desirably antigenic.

Several means are now used on large scale to achieve the desired disruption of viruses into sub-units. These comprise generally the use, on the one hand, of detergents or, on the other, ether, a volatile highly-flammable substance. A detergent-disrupted, sub-unit vaccine prepared by sodium desoxycholate treatment, of influenza viruses is commercially available but suffers from considerably reduced immunogenicity (as measured by mouse potency tests) as compared with the intact viruses (Rubin et al., Arch. Virus-forsch., 20:268 [1967]; Webster, J. Immunol., 96:596 [1966]). Another important proposal has been to use ether as a disrupting agent. However, contrary to some claims in the literature, and as will be shown in the drawing, ether does not nearly completely eliminate toxicity as measured by standard pyrogenicity tests in rabbits. Furthermore, ether can cause a substantial loss of the enzyme, neuraminidase. This is disadvantageous because it has been suggested that the best vaccines must contain good levels of this enzyme. Therefore, it would be desirable to provide means to disrupt viruses, especially influenza viruses, into sub-units, which means are more effective than ether for removing pyrogens, without at the same time causing substantial losses of neuraminidase, and which do not reduce the potency of the virus as an immunizing agent, as do detergents such as sodium desoxycholate. It is also desirable to provide means to disrupt concentrated viruses as well as impure allantoic fluids. Surprisingly, such means for the disaggregation of viruses are provided by the method of the instant invention.

It is, therefore, a primary object of the instant invention to provide methods to disrupt viruses.

It is another object of the instant invention to provide a means to disrupt viruses at the same time lowering toxicity and pyrogenicity.

Still another object of the instant invention is to provide a means to disrupt viruses without at the same time lowering significantly the neuraminidase level.

It is a further object of the instant invention to provide methods to disrupt viruses without substantially decreasing the immunogenicity thereof as compared with intact viruses.

Still another object of the instant invention is to provide a means to disrupt viruses which can be employed in large scale manufacturing facilities without danger from explosion or fire.

Still another object of the instant invention is to provide disrupted viruses useful to prepare vaccines for diagnostic and immunogenic purposes.

DESCRIPTION OF THE INVENTION

All of the above advantages and objects may readily be secured by practice of the process of the instant invention which is, in essence: In a method for the disruption of viruses, the step of bringing the intact virus in an aqueous medium into contact with a wetting agent and a trialkyl phosphate wherein said alkyl groups contain from 4 to 10 carbon atoms.

Special mention is made of a number of important embodiments of this invention which are, respectively:

a method as above defined wherein the aqueous medium and disrupted viruses are separated from said trialkyl phosphate;

a method as above defined wherein said viruses are influenza or rabies viruses;

a method as above defined wherein said wetting agent is a polyoxyethylene sorbitan higher fatty acid partial ester;

a method as above defined wherein said trialkyl phosphate is tri-(n-butyl) phosphate;

in a method for the disruption of influenza viruses in an allantoic fluid, the steps of bringing the intact virus in said fluid into contact with tri-(n-butyl) phosphate dispersed in said fluid with polyoxyethylene sorbitan mono-oleate, and separating the fluid and disaggregated virus from the said trialkyl phosphate;

a method as next above defined wherein said virus is Type $A_2$/Taiwan, Type B/Massachusetts or Type $A_2$/Japan 170;

in a method for the disruption of viruses, the steps of bringing intact virus in an aqueous medium into contact on a calcium phosphate chromatographic column with a wetting agent and a trialkyl phosphate wherein said alkyl groups contain from 4 to 10 carbon atoms, and eluting with phosphate buffer having a pH of from about 6 to about 8.

When used herein and in the appended claims the term "virus" contemplates infectious lipid-containing viruses such as influenza virus and also rabies virus, Newcastle disease virus, mumps virus, pneumonia virus of mice, eastern equine encephalomyelitis virus, Saint Louis encephalitis virus, Japanese encephalitis virus, yellow fever virus, dengue virus, West Nile virus, Theile GD VII virus, encephalomyocarditis virus, lymphocytic chorimeningitidis virus, vesicular stomatitis virus, and the like. The aqueous medium containing the intact viruses can be any type of fluid from which those skilled in the art commonly isolate or propagate viruses such as, for example, allantoic fluid, tissue culture fluid, an aqueous extract or suspension of central nervous system tissue, blood cell eluate, an aqueous extract or suspension of fowl embryo and the like. The antigenic potency of the virus solution used as a starting material is not critical and can be varied as desired. For influenza virus, for example, a suitable intact virus medium for use in practicing the instant invention, would be the allantoic fluid obtained by pooling 11-day old impregnated chick eggs inoculated with influenza virus (for example of Type A, A-1, A-2 or B; for example the Pr-8, Ann Arbor, Asian, Taiwan, Japan/170, B/Mass., or Great Lakes strains, respectively) and incubated for 48 hours at about 35°C. In the production of the vaccines of influenza it is general practice to inoculate eggs in batches of about 20,000. The viruses are developed in the allantoic fluids of the infected eggs. After the proper incubation time the eggs are broken and the fluids centrifuged through a high speed centrifuge. The viruses are drawn out of the liquid along with considerable amounts of egg protein and the like. The resulting sediment is resuspended in saline and can be ball-milled for about 12–15 hours to give an aqueous virus suspension which is then cleared in a low speed centrifuge to give a virus concentrate. As is mentioned above, surprisingly, the instant method can use as starting material either the pooled allantoic fluid or the virus concentrate.

The particular solvent required by the instant process is a "trialkyl phosphate wherein said alkyl groups contain from 4 to 10 carbon atoms." This contemplates a particular class of organic solvents which can act on aqueous suspensions of viruses to provide the desired disruption in an unexpectedly efficient manner, lowering toxicity at the same time. These esters are substantially water insoluble in the sense that the class includes dispersible materials which dissolve to the extent of no more than about 1 gram in 100 grams of water at 25°C. Particularly useful phosphate esters, therefore, are those derived from aliphatic straight and branched chain alcohols containing from 4 to 10 carbon atoms, illustrative members of which are tri-(n-butyl) phosphate, tri-(t-butyl) phosphate, tri-(n-hexyl) phosphate, tri-(2-ethylhexyl) phosphate, tri-(n-decyl) phosphate, and the like. An especially preferred phosphate ester is tri-(n-butyl) phosphate. It is critical to the process to incorporate in the medium a wetting agent, and preferably nonionic wetting agents. The wetting agent does not itself affect the virus; it is needed merely to enhance contact of the virus with the phosphate ester. Preferred wetting agents are polyoxyethylene sorbitan higher fatty acid partial esters, illustrative members of which are polyoxyethylene sorbitan monolaurate and mono-oleate, both of which are available commercially (under the tradenames, "Tween 20" and "Tween 80", respectively). As will be illustrated hereinafter. a particularly important practical embodiment of this invention is the disruption of influenza viruses both of Types A and B.

In carrying out the instant process, which, as has been stated above, is applicable to virus containing media generally but for purposes of illustration is described hereinafter with particular reference to media containing influenza virus, the disruption can be achieved by subjecting the virus solution undiluted or concentrated to phosphate ester extraction. In this procedure the virus solution is mixed with phosphate ester, preferably from about 1 to 30 parts of solution per part by volume of ester, and for best results at a temperature of between about 4°C. and about 25°C. for a sufficient time to allow for substantially complete breakdown of the virus particles. Phosphate ester treatment disrupts the intact influenza virus particle into smaller lipid-free particles (sub-units) carrying all of the surface antigens of the intact viruses. The preferred mixing time is about one hour for influenza virus, although times as short as 3 minutes and much longer than 1 hour can be used. Following the mixing step the aqueous and phosphate ester phases are allowed to separate, preferably in the cold, and the aqueous phase containing the desired sub-unit virus antigen is recovered. In any event, if allantoic fluid has been used, phase separation is facilitated by the addition of paraffin oil, about 1% by volume to the virus solution after phosphate ester treatment. Extraction of the aqueous phase with phosphate ester must be carried out with a wetting agent incorporated in the aqueous phase, otherwise the desired results are not obtained. Nonionic wetting agents are particularly suitable for this purpose. Preferred wetting agents are the polyoxyethylene sorbitan higher fatty acid partial esters such as polyoxyethylene sorbitan monolaurate and mono-oleate. The amount employed is not particularly critical, for example, from about 0.01 to about 1% can be used, but it is convenient to use about 0.1% of wetting agent, based on the aqueous fluid weight. The resulting extracts which are non-infectious, can be used for the preparation of vaccines or diagnostic agents or can be used to inject animals for the preparation of specific antisera and the like. In the case of vaccine preparation, for example, a suitable influenza virus vaccine is obtained either by bacteriological sterile filtration (an advantage compared with the prior art) or, by conventional means, as by adding a preservative such as thimerosal (1:10,000) and a stabilizer such as formalin. The optimum concentration for stabilization is about 0.1%.

The extracts prepared by this invention are especially suitable as starting materials for influenza virus chromatographic purification processes. Merely by way of illustration, increased purification over all conventional means will be obtained by washing calcium dihydrogen orthophosphate monohydrate, with water, then with alkali so as to adjust its pH to about 6.5, then washing with water until the pH is raised to about pH 7.2 – 7.4, then washing with an alkali metal trimetaphosphate (TMP) solution, to a pH of about 8.0 and introducing to a chromatographic column and washing with TMP to pH 8 – 8.1. Then a virus-containing extract prepared according to this invention, diluted if desired, said virus having been treated with an alkali metal trimetaphosphate at a pH of about 8.0 is poured onto the column. The column is washed with 0.01 TMP buffer, pH 8.0, then is eluted with a buffer, i.e., a 1.0 M phosphate buffer, having a pH of about 5.0 – 9.0. It is preferred to elute Type A influenza at pH 6.0 and Type B influenza at pH 8.0. The eluates can then be formulated by entirely conventional means, such as those described above, into exceptionally useful vaccines.

In a praticularly preferred embodiments of the invention, the virus is disrupted and purified in essentially one operation on a chromatographic column. In this embodiment, the virus-containing medium, for example, infected allantoic fluid, is applied without further treatment to a calcium phosphate chromatographic column, the column is washed with a dilute sodium trimetaphosphate solution containing the wetting agent and the trialkylphosphate, and the virus is eluted with phosphate buffer containing additional wetting agent and trialkylphosphates. The eluate thus obtained contains the disrupted virus substantially free of non-viral protein, and is suitable for formulation into superior vaccines. As desired, the eluate may be further purified by means well known in the art, such as dialysis, to decrease the concentration of salts, trialkylphosphate, and wetting agent to desirable levels for use in vaccines. In this embodiment, the trialkylphosphate concentration in the disruption and elution media is preferably 0.3%, although concentrations of from 0.1% to slightly more than 1% can be used. The preferred phosphate ester is tri-n-butylphosphate. The wetting agent concentration can be varied from about 0.05% to about 0.25%, although 0.1% is preferably. Tween 80 is a preferred wetting agent. The pH of the phosphate buffer elution medium can be varied from about 6 to about 8. The optimum pH within this range will vary with the particular virus concerned; for example, pH 6 is optimum for Type A influenza virus and pH 8 is optimum for Type B. The elution is accomplished using a buffer concentration of about 1 molar, or by gradient elution between about 0.1 to about 1.0 molar.

In another particularly preferred embodiment, a rabies vaccine may be simply prepared by treatment of crude infectious tissue culture fluid according to the process of the invention, without any need for separation of the aqueous medium and disrupted viruses from the trialkylphosphate. In this embodiment, an aqueous suspension of tissue culture fluid infected with rabies virus is treated with a concentration of trialkylphosphate sufficient to cause disruption of the virus, yet sufficiently low so that no phase separation will occur. Where tri-(n-butyl) phosphate is used, treatment of the tissue culture fluid with 0.1% of the phosphate and 0.1% polyoxyethylene sorbitan monooleate at 37° for sufficient length of time to disrupt the rabies virus, not more than 144 hours, will provide a single phase non-infectious product suitable for use as a vaccine without further separation or purification.

Pyrogenicity tests in laboratory animals are a standard means to measure toxicity of virus suspensions. One widely used procedure is to inject small amounts of the test fluid into rabbits and to measure the body temperature at 15 minute intervals. The test is carried out over an eight hour period and virus suspensions which contain undesirable toxic materials cause the temperature of the animal to increase. With untreated solutions of viruses, it is usual to observe elevations of 2°C. or more. It is an accepted practice to treat virus solutions with formaldehyde which lowers the temperature increase somewhat but not completely to normal. Furthermore, extraction of virus solutions with ether also has a tendency to lower the temperature increase. But with the instant invention, the effect of reducing the pyrogenicity of the virus suspension is particularly marked in comparison with the prior art methods.

This effect is illustrated in the accompanying drawing, FIGS. 1–3 in which:

FIG. I shows the temperature response of rabbits injected with doses of aqueous influenza virus Type A-2/Taiwan, 4000 hemagglutinating (HA) units/ml. — untreated, formalinized, ether-treated and treated with tri-(n-butyl)phosphate according to this invention.

FIG. 2 shows the temperature response of rabbits injected with aqueous influenza virus Type B/Mass., — untreated, formalinized. ether-treated, and treated with tri-(n-butyl) phosphate according to this invention.

FIG. 3 shows the temperature response of rabbits injected with aqueous influenza virus Type $A_2$/-Japan/170 — untreated, formalinized, ether-treated, and treated with tri-(n-butyl)phosphate according to this invention.

A comparison of the temperature levels shown on these Figures in the various lines, shows that in each virus-containing fluid, treatment with tri-(n-butyl)-phosphate if far more effective in lowering the pyrogens than is treatment with ether, and, especially in the period after about 3 hours, it is more effective than is treatment with formalin.

DESCRIPTION OF THE PREFERRED EMBODIMENTS

The following examples illustrate the process of the instant invention. They are merely to show ways to use the invention but are not to be construed to limit the scope thereof in any manner whatsoever.

EXAMPLE 1

A centrifugate starting material is prepared as follows: 11-day old embryonated chick eggs are inoculated with influenza virus [either of Type A or B; respectively, A-2/Japan/170; A-2/Taiwan and B/Mass.] and incubated for 48 hours at 35°C. Following incubation, the allantoic fluid is collected, centrifuged and the resulting sediment is resuspended in saline and ball-milled for 12 to 15 hours. The resulting aqueous virus suspension is then cleared in a low speed centrifuge.

Polyoxyethylene sorbitan mono-oleate (Tween 80) is added to each virus concentrate in a concentration of one mg./ml. (0.1%). One hundred parts by volume of the resulting mixture is combined with 3.3 parts by volume of tri-(n-butyl)phosphate and the resulting aqueous tri-(n-butyl)phosphate mixture is stirred at 23°C. for about 1 hour at a rate such that no foaming occurs and yet no separation of the two phases takes place. The aqueous and tri-(n-butyl)phosphate phases are then allowed to separate during about 16 hours, the tri-(n-butyl)phosphate layer is removed and the aqueous phase is collected. The resulting aqueous antigen products are more than 99.9% reduced in infectivity and can be used for immunogenic, prophylactic or diagnostic purposes. For example, vaccines having low pyrogenicity can be prepared from the aqueous products adjusting to desired immunogenic potency with deionized water followed by sterile filtration

EXAMPLE 2

The procedure of Example 1 is repeated, substituting for the centrifugate, the impure pooled allantoic fluids containing Type $A_2$/Taiwan. Type $A_2$/Japan/170 and Type B/Mass. When the extraction is terminated, this time there is added 1% by volume of paraffin oil to facilitate phase separation. Phase separation in this case is made by centrifugation. The aqueous phase can be made up into superior vaccines by the procedure of Example 1. However, especially highly effective vaccines are provided if the following steps are taken:

One hundred grams of calcium phosphate monobasic monohydrate [$Ca(H_2PO_4)_2.H_20$] and 400 ml. of deionized water are stirred vigorously for 15 minutes. pH 2.3. Under conditions of continuous mixing, a cold (4°C.) 3N sodium hydroxide solution is added dropwise over a period of one-half hour until a pH of 6.5 is reached. The contents of the reaction mixture is kept at 20°–23°C. by an external ice bath. After stirring for one-half hour, the adsorbent is permitted to settle and the supernatant liquid is decanted. The adsorbent is washed batchwise with one-half liter portions of deionized water until the pH of the supernatant liquid is 7.2–7.4. The adsorbent is then batch washed with a buffered 0.01 M sodium trimetaphosphate (pH 9.0) solution until a pH of 8.0 is reached (four, 500-ml. portions).

One-hundred grams of $Ca(H_2PO_4)_2.H_2O$ treated as described is placed in a glass column containing a sintered glass disk to support the bed and washed with TMP buffer to an effluent pH of 8.0. To the column there is delivered 750 ml. of infected allantoic fluid containing the ester-extracted virus, diluted with an equal volume of sterile distilled water. The diluted fluid has been adjusted to pH of 8.0 with 0.01M sodium trimetaphosphate and flows through the column over a period of two hours. The column is then washed with 200 ml. of 0.01M sodium trimetaphosphate (pH 8) solution and the Type A virus eluted with 0.1M phosphate buffer (pH 6.0) and Type B virus eluted with 0.1M phosphate buffer (pH 8.0).

By the above procedure a high recovery of the virus strain is obtained at a good purification factor. This can be formulated into superior vaccines by the method of Example 1. Vaccines containing, respectively, influenza viruses Type $A_2$/Taiwan, Type B/Mass. and Type $A_2$/Japan/170 are thus obtained.

EXAMPLE 3

The procedure of Example 1 is repeated substituting influenza viruses of the following strains: A/PR-8; A/Jap 305; A/Ann Arbor; B/Great Lakes and B/Maryland. Substantially the same results are obtained.

The procedure of Example 1 is repeated substituting for the tri-(n-butyl)phosphate, equal volumes, respectively, of tri-(t-butyl)phosphate, tri-(n-hexyl)phosphate, tri-(2-ethylhexyl)phosphate and tri-(n-decyl)phosphate. With all of these esters, the chromatographic steps of Example 2 are desirable to remove traces of ester from the aqueous phase. Substantially the same results are obtained.

The procedure of Example 1 is repeated, substituting for the polyoxyethylene sorbitan mono-oleate an equal volume of polyoxyethylene sorbitan monolaurate. Substantially the same results are obtained.

EXAMPLE 4

The procedure of Example 1 is repeated, substituting for the centrifugate of influenza-infected allantoic fluid, an aqueous suspension of tissue culture fluid infected with rabies virus. A purified, sub-unit antigenic product is obtained.

EXAMPLE 5

One hundred grams of calcium phosphate monobasic monohydrate [$Ca(H_2PO_4)_2.H_2O$] and 400 ml. of deionized water are stirred vigorously for 15 minutes. Under conditions of continuous mixing, a cold (4°C.) 3N sodium hydroxide solution is added dropwise over a period of one-half hour until a pH of 6.5 is reached. The contents of the reaction mixture is kept at 20°–23°C. by an external ice bath. After stirring for one-half hour, the adsorbent is permitted to settle an the supernatant liquid is decanted. The adsorbent is washed batchwise with one-half liter portions of deionized water until the pH of the supernatant liquid is 7.2–7.4. The adsorbent is then batch washed with a buffered 0.01 M sodium trimetaphosphate (pH 9.0) solution until a pH of 8.0 is reached (four, 500-ml. portions).

One hundred grams of $Ca(H_2PO_4)_2.H_2O$ treated as described is placed in a glass column containing a sintered glass disk to support the bed and washed with TMP buffer to an effluent pH of 8.0. To the column there is delivered 750 ml. of infected allantoic fluid containing the virus, diluted with an equal volume of sterile distilled water, and made 0.01 M in sodium trimetaphosphate (3.00 g/1). The column is then washed with 100 ml. of 0.01 sodium trimetaphosphate (pH 8) and subsequently with 0.01 M sodium trimetaphosphate containing in addition 0.1% Tween 80 and 0.3% tri-n-butyl-phosphate. The Type A virus is eluted with 1.0 M phosphate buffer (pH 6.0) containing 0.1% Tween 80 and 0.3% tri-n-butylphosphate, and the Type B virus is eluted with 1.0 M phosphate buffer (pH 8.0) containing 0.1% Tween 80 and 0.3% tri-n-butylphosphate.

By the above procedure a high recovery of the disrupted virus, freed from 98% of the non-viral protein originally present, is obtained.

EXAMPLE 6

Aqueous tissue culture fluid containing infectious rabies virus is treated with tri-(n-butyl)phosphate at a concentration of 0.1% and polyoxyethylene sorbitan monooleate at a concentration of 0.1% and polyoxyethylene sorbitan monooleate at a concentration of 0.1% at 37° for 48 hours. The resulting product is a homogeneous suspension, free of infections virus, and may be used directly as a vaccine.

The subject matter which applicant regards as his invention is particularly pointed out and distinctly claimed as follows:

1. In a method for the disruption of infectious lipid-containing viruses for preparing sub-unit vaccines, the step of bringing the intact infectious lipid-containing virus in an aqueous medium into contact with effective amounts of a wetting agent and a trialkylphosphate wherein said alkyl groups contain from 4 to 10 carbon atoms.

2. A method as defined in claim 1 wherein said viruses are rabies viruses.

3. A method as defined in claim 1 wherein said viruses are rabies viruses and said trialkylphosphate is tri-(n-butyl)phosphate.

4. In a method for the disruption of infectious lipid-containing viruses for preparing sub-unit vaccines, the steps of bringing the intact infectious lipid-containing virus in an aqueous medium into contact with effective amounts of a wetting agent and a trialkylphosphate wherein said alkyl groups contain from 4 to 10 carbon atoms, and separating the aqueous medium and disrupted virus from the said trialkylphosphate.

5. A method as defined in claim 4 wherein said viruses are influenza viruses.

6. A method as defined in claim 4 wherein said viruses are rabies viruses.

7. A method as defined in claim 4 wherein said wetting agent is a polyoxyethylene sorbitan higher fatty acid partial ester.

8. A method as defined in claim 4 wherein said trialkylphosphate is tri-)n-butyl)phosphate.

9. In a method for the disruption of influenza viruses in an allantoic fluid, for preparing sub-unit vaccines, the steps of bringing the intact virus in said fluid into contact with an effective amount of tri-(n-butyl)phosphate dispersed in said fluid with an effective amount of polyoxyethylene sorbitan mono-oleate, and separating the fluid and disrupted virus from the said trialkyl phosphate.

10. A method as defined in claim 9 wherein said influenza virus is Type $A_2$/Taiwan.

11. A method as defined in claim 9 wherein said influenza virus is Type B/Massachusetts.

12. A method as defined in claim 9 wherein said influenza virus is Type $A_2$/Japan/170.

13. In a method for the disruption of infectious lipid-containing viruses for preparing sub-unit vaccines, the steps of bringing the intact infectious lipid-containing virus into contact on a calcium phosphate chromatographic column with an aqueous solution containing effective amounts of from about 0.05 to about 0.25% by weight of a wetting agent and from about 0.1% to about 1% by volume of a trialkylphosphate wherein said alkyl groups contain from 4 to 10 carbon atoms, and eluting with phosphate buffer having a pH of from about 6 to about 8.

14. A method as defined in claim 13 wherein said trialkylphosphate is tri-(n-butyl)phosphate.

15. A method as defined in claim 14 wherein said viruses are influenza viruses.

16. A method as defined in claim 1 wherein said viruses are rabies viruses, wherein the wetting agent is polyoxyethylene sorbitan mono-oleate in about 0.1% concentration, and the trialkylphosphate is tributylphosphate in about 0.1% concentration.

* * * * *